(12) United States Patent
Li et al.

(10) Patent No.: US 12,076,398 B2
(45) Date of Patent: Sep. 3, 2024

(54) ANTI-PD1 MONOCLONAL ANTIBODY, PHARMACEUTICAL COMPOSITION THEREOF AND USE THEREOF

(71) Applicant: CTTQ-AKESO (SHANGHAI) BIOMED. TECH. CO., LTD., Shanghai (CN)

(72) Inventors: Baiyong Li, Guangdong (CN); Yu Xia, Guangdong (CN); Zhongmin Maxwell Wang, Guangdong (CN); Peng Zhang, Guangdong (CN)

(73) Assignee: CTTQ-AKESO (SHANGHAI) BIOMED. TECH. CO., LTD., Shanghai (CN)

( * ) Notice: Subject to any disclaimer, the term of this patent is extended or adjusted under 35 U.S.C. 154(b) by 59 days.

(21) Appl. No.: 16/327,083

(22) PCT Filed: Aug. 22, 2017

(86) PCT No.: PCT/CN2017/098465
§ 371 (c)(1),
(2) Date: Feb. 21, 2019

(87) PCT Pub. No.: WO2018/036472
PCT Pub. Date: Mar. 1, 2018

(65) Prior Publication Data
US 2019/0321466 A1    Oct. 24, 2019

(30) Foreign Application Priority Data

Aug. 23, 2016   (CN) .......................... 201610705763.5

(51) Int. Cl.
| A61K 39/395 | (2006.01) |
| A61P 35/02 | (2006.01) |
| C07K 16/28 | (2006.01) |
| G01N 33/577 | (2006.01) |
| G01N 33/68 | (2006.01) |

(52) U.S. Cl.
CPC ............ *A61K 39/395* (2013.01); *A61P 35/02* (2018.01); *C07K 16/28* (2013.01); *G01N 33/577* (2013.01); *G01N 33/68* (2013.01)

(58) Field of Classification Search
None
See application file for complete search history.

(56) References Cited

U.S. PATENT DOCUMENTS

| 10,066,013 | B2 | 9/2018 | Chen et al. | |
| 11,578,128 | B2 * | 2/2023 | Li .......................... | A61P 35/00 |
| 2015/0093380 | A1 | 4/2015 | Honjo et al. | |
| 2017/0216433 | A1 | 8/2017 | Li et al. | |
| 2019/0161548 | A1 | 5/2019 | Johnson et al. | |
| 2019/0177414 | A1 | 6/2019 | Li et al. | |
| 2019/0185569 | A1 | 6/2019 | Li et al. | |

FOREIGN PATENT DOCUMENTS

| CN | 1753912 B | 3/2006 |
| CN | 104974253 A | 10/2015 |
| CN | 104987421 A | 10/2015 |
| CN | 105175544 A | 12/2015 |
| CN | 105175545 | * 12/2015 |
| CN | 105175545 A | 12/2015 |
| CN | 105754990 A | 7/2016 |
| CN | 106967172 A | 7/2017 |
| CN | 106977602 A | 7/2017 |
| KR | 20160058938 A | 5/2016 |
| WO | WO 2009/134776 A2 | 11/2009 |
| WO | WO 2009/134776 A3 | 11/2009 |
| WO | WO 10/036959 A2 | 4/2010 |
| WO | WO 11/113019 A2 | 9/2011 |
| WO | WO 2012/120125 A1 | 9/2012 |
| WO | WO 12/145493 A1 | 10/2012 |
| WO | WO 2012135408 | 10/2012 |
| WO | WO 14/022758 A1 | 2/2014 |
| WO | WO 2014/209804 A1 | 12/2014 |
| WO | WO-2015048520 A1 | 4/2015 |
| WO | WO 2015/085847 A1 | 6/2015 |
| WO | WO 2015/101587 A1 | 7/2015 |
| WO | WO 2015/112800 A1 | 7/2015 |
| WO | WO 2016/015675 A1 | 2/2016 |
| WO | WO 2016/180034 A1 | 11/2016 |
| WO | WO 2017/106061 A1 | 6/2017 |
| WO | WO 2017/128534 A1 | 8/2017 |
| WO | WO 2018/036472 A1 | 3/2018 |
| WO | WO 2018/036473 A1 | 3/2018 |

OTHER PUBLICATIONS

CN105175545a, Hu et al., published Dec. 23, 2015, English translation.*
Okawa et al (Intern Med 58: 699-702, 2019).*
Tanios (Blood (2018) 132 (Supplement 1): 2324).*
Monnier et al (Antibodies, 2013, 2:193-208).*
Kontermann (Bispecific Antibodies, Springer Berlin, Heidelberg, 2011).*
Mazor et al (Scientific Reports, 2017, 7:40098).*
Lu et al (Recombinant Technology, 2002, 267:213-226).*
Orcutt et al (Protein Engineering, Design, & Selection, 2009, 23:221-228).*

(Continued)

*Primary Examiner* — Laura B Goddard
(74) *Attorney, Agent, or Firm* — COOLEY LLP; Chen Chen; Robert E. Powers

(57) ABSTRACT

An anti-PD1 (programmed cell death 1) monoclonal antibody or an antigen-binding fragment thereof, a pharmaceutical composition thereof and use thereof. The heavy chain variable region of the monoclonal antibody comprises CDRs (complementary determining region) of amino acid sequences as shown in SEQ ID NO:9-11; and/or the light chain variable region of the monoclonal antibody comprises CDRs of amino acid sequences as shown in SEQ ID NO: 12-14. The monoclonal antibody can bind to PD1 specifically, relieve immunosuppression of PD1 on an organism specifically and activate T lymphocytes.

6 Claims, 6 Drawing Sheets
Specification includes a Sequence Listing.

(56) References Cited

OTHER PUBLICATIONS

International Search Report based on International Patent Application No. PCT/CN2017/098466, dated Nov. 14, 2017, 12 pages includes English translation.
International Search Authority Written Opinion based on International Patent Application No. PCT/CN2017/098466, dated Nov. 14, 2017, 5 pages (Non-English).
English Translation of International Search Authority Written Opinion based on International Patent Application No. PCT/CN2017/098466, dated Nov. 14, 2017, 6 pages.
International Search Report based on International Patent Application No. PCT/CN2017/098465 dated Oct. 31, 2017, 12 pages including English translation.
International Search Authority Written Opinion based on International Patent Application No. PCT/CN2017/098465, dated Oct. 27, 2017, 5 pages (Non-English).
English Translation of International Search Authority Written Opinion based on International patent Application No. PCT/CN2017/098465, dated Oct. 27, 2017, 6 pages.
Chan et al., "Abstract 5021: Regulatory T-Cells and Effects of Anti-CTLA4 and anti-PD1 Therapy in a Transgenic Murine Model of Neuroblastoma," Proceedings: AACR Annual Meeting 2014; Apr. 5-9, 2014; San Diego, CA, 4 pages, retrieved May 22, 2019 at http://cancerres.aacrjournals.org/content/74/19_Supplement/5021.
Blatter et al.,"Abstract 736: Combining PD1- and CTLA4-inhibiting antibodies with cisplatin or PARP inhibition in an attempt to eradicate BRCA1-deficient mouse mammary tumors," Cancer Research , AACR 106th Annual Meeting 2015; Apr. 18-22, 2015; Philadelphia, PA, 4 pages retrieved May 22, 2019 at http://cancerres.aacrjournals.org/content/75/15_Supplement/736.
Miao et al., "Role of Programmed Death-I PD-1 in Patients with Aplastic Anemia," Jiangsu Medical Journal, pp. 626-627 (2009).
Orcutt et al., "A modular IgG-scFv bispecific antibody topology," Protein Engineering, Design & Selection : Peds APR 23(4):221-228 (2010).
Brahmer et al., "Nivolumab: targeting PD-1 to bolster antitumor immunity," Future Oncology 11(9):1307-1326 (2015).
McDermott et al., "Pembrolizumab: PD-1 inhibition as a therapeutic strategy in cancer," Drugs of Today 51(1):7-20 (2015).
Anonymous: "Study of REGN2810 (Anti-PD-1) in Patients With Advanced Malignancies—Full Text View—ClinicalTrials.gov", Mar. 9, 2015, Retrieved from the Internet: URL:https://clinicaltrials.gov/ct2/show/NCT02383212 [retrieved on Mar. 5, 2020], 8 pages.
Altshuler et a. "Generation of recombinant antibodies and methods for increasing their affinity", Biochemistry, 70(13):1584-1605 (2010).
Hoogenboom, H., "Selecting and screening recombinant antibody libraries", Nature Biotechnology 23(9):1105-1116 (2005).
He, M., et al., "Remarkably similar CTLA-4 binding properties of therapeutic ipilimumab and tremelimumab antibodies," Oncotarget, May 19, 2017, vol. 19; 8(40), p. 67129-67139.
Inbal Sela-Culang, et al., "The Structural Basis of Antibody-Antigen Recognition," Frontiers in Immunology, vol. 4, Oct. 8, 2013, ,DOI: 10.3389/fimmu.2013.00302,span p. 7./span.
Nair et al., "Immunotherapy-associated hemolytic anemia with pure red-cell aplasia." New England Journal of Medicine 374(11):1096-1097 (Mar. 17, 2016).
Philips, G. K. et al., "Therapeutic uses of anti-PD-1 and anti-PD-L1 antibodies," International Immunology, vol. 27, No. 1, Oct. 2014, pp. 39-46.
Sun, L., et al., "Targeting Glycosylated PD-1 Induces Potent Anti-tumor Immunity", Cancer research, vol. 80, No. 11, Jun. 1, 2020, pp. 2298-2310.
Tan, S., "An unexpected N-terminal loop in PD-1 dominates binding by nivolumab," Nature communications. vol. 8, 14369, pp. 1-10 (Feb. 6, 2017).

* cited by examiner

ANTI-PD1 MONOCLONAL ANTIBODY, PHARMACEUTICAL COMPOSITION THEREOF AND USE THEREOF

CROSS-REFERENCE TO RELATED APPLICATIONS

This application is a U.S. National Phase of PCT/CN2017/098465, filed Aug. 22, 2017, which claims priority to Chinese Patent Application No. 201610705763.5, filed Aug. 23, 2016, each of which is hereby incorporated by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: AKSO_003_01US_SubSeqList_ ST25. txt, date created: Jan. 29, 2024, file size 12,924 bytes).

TECHNICAL FIELD

The present invention belongs to the field of tumor therapy and molecular immunology, relating to an anti-PD1 antibody, the pharmaceutical composition and methods of use. Specifically, the present invention relates to an anti-PD1 monoclonal antibody.

TECHNICAL BACKGROUND

The transmembrane receptor PD1 (programmed cell death 1, also known as PD-1) is a member of the CD28 gene family, expressed in activated T cells, B cells and myeloid cells. Both ligands of PD1 (i.e. PDL1 and PDL2) belong to the B7 superfamily; wherein PDL1 is broadly expressed in a variety of cells including T cells, B cells, endothelial cells and epithelial cells, while PDL2 is only expressed in antigen presenting cells such as dendritic cells and macrophages.

T cells play a very important role in the elimination of viral infections, and T cell antiviral response is usually associated with immunopathogenesis. PD1 plays a vital role in the negative regulation of T cell activation. Although PD1-mediated negative regulation on T cells can reduce tissue damage caused by infection, blocking or inhibiting the negative regulatory effect of PD1 may lead to autoimmune diseases, for example, pancreatic virus infection can be more effectively eliminated in PD1 gene knockout mice, but may lead to more severe liver damage (Isai et al., 2003, J.Exp.Med. 198:39-50). In addition, tumors with highly expressed PD1 often develop into cancers that are difficult to detect (Hamanishi et al., 2007, Proc.Natl.Acad.Sci.USA 104:3360-5). An established method to regulate PD1 expression is through injection of antibodies into the body.

Due to the broad antitumor prospects and astounding efficacy of PD1 antibody, it is generally believed that antibodies against PD1 pathways will lead to breakthroughs in the treatment of a variety of tumors: non-small cell lung cancer, renal cell carcinoma, ovarian cancer, melanoma (Homet M. B., Parisi G., et al., Anti-PD1 Therapy in Melanoma. Semin Oncol. 2015 June; 42(3):466-473), leukemia, and anemia (Held S A, Heine A, et al., Advances in immunotherapy of chronic myeloid leukemia CML. Curr Cancer Drug Targets. 2013 September; 13(7):768-74).

Ever since the revelation of the unprecedented clinical efficacy data at the annual meetings of American Association for Cancer Research (AACR) and American Society of Clinical Oncology (ASCO) in 2012 and 2013, PD1 antibodies have become the hottest new drugs in R&D in the global pharmaceutical industry.

At present, there is still a need to develop new anti-PD1 antibodies with better binding efficiency to effectively block the binding of PD1 to PDL1.

SUMMARY OF THE INVENTION

Through in-depth research and creative work, by immunizing mice with recombinant PD1 expressed in mammalian cells expression system as antigen, the inventors obtained hybridoma cells via fusion of mouse splenocytes and myeloma cells. By screening a large number of samples, the inventors obtained the hybridoma cell line LT003 (CCTCC Deposit Accession No.: C2015105).

The inventors surprisingly found that the hybridoma cell line LT003 is capable of secreting a specific monoclonal antibody (named 14C12) binding specifically to PD1, and this monoclonal antibody can effectively block the association of PD1 to PDL1.

Furthermore, the inventors generated a humanized anti-PD1 antibody (named 14C12H1L1) in a creative way.

More surprisingly, the inventors found that the antibodies 14C12 and 14C12H1L1 herein can effectively bind to human T cells, activate T cells and induce the secretion of IFN-γ and IL-2 from human lymphocytes. The antibodies 14C12 and 14C12H1L1 herein have the potential to become drugs for preventing and treating malignancies including lung cancer, melanoma, renal cancer, ovarian cancer and leukemia, as well as anemia.

The following are provided by the present invention:
The present invention relates to a monoclonal antibody or its antigen-binding fragments thereof, wherein,
  the heavy chain variable region ($V_H$) of the said monoclonal antibody comprises: CDRs with the amino acid sequences of SEQ ID NO:9-11;
  and/or
  the light chain variable region ($V_L$) of the said monoclonal antibody comprises: CDRs with the amino acid sequences of SEQ ID NO:12-14.

In some examples of the present invention, the said monoclonal antibody or its antigen-binding fragments thereof, wherein,
  the amino acid sequence of $V_H$ of the monoclonal antibody is chosen from SEQ ID NO:2 and SEQ ID NO:6;
  and/or
  the amino acid sequence of $V_L$ of the monoclonal antibody is chosen from SEQ ID NO:4 and SEQ ID NO:8.

In an example of the present invention, the said monoclonal antibody or its antigen-binding fragments thereof, wherein, the monoclonal antibody comprises:
  (1) $V_H$ shown by SEQ ID NO:2 and $V_L$ shown by SEQ ID NO:4;
  (2) $V_H$ shown by SEQ ID NO:6 and $V_L$ shown by SEQ ID NO:8.

The variable regions in heavy and light chains of an antibody govern binding activity. Each chain contains three hypervariable regions, namely, the complementary determining region (CDR) (HCDR1, HCDR2 and HCDR3 in heavy (H) chain, and LCDR1, LCDR2 and LCDR3 in light (L) chain), which are defined by Kabat, et al. (Sequences of Proteins of Immunological Interest, Fifth Edition (1991), volume 1-3, NIH Publication 91-3242, Bethesda MD).

Through techniques well-known to technical personnel in the field described herein, for example, analyzing the amino acid sequences in the CDR of the monoclonal antibody sequences in Items (1) and (2) above through VBASE2 database:

The antibodies 14C12 and 14C12H1L1 herein comprises the same CDR:

Wherein the amino acid sequences of the 3 CDR regions of $V_H$ are as follows:

HCDR1:
(SEQ ID NO: 9)
GFAFSSYD,

HCDR2:
(SEQ ID NO: 10)
ISGGGRYT,

HCDR3:
(SEQ ID NO: 11)
ANRYGEAWFAY;

Wherein the amino acid sequences of the 3 CDR regions of $V_L$ are as follows:

LCDR1:
(SEQ ID NO: 12)
QDINTY,

LCDR2:
(SEQ ID NO: 13)
RAN,

LCDR3:
(SEQ ID NO: 14)
LQYDEFPLT.

In certain example, the said monoclonal antibody or its antigen-binding fragment thereof, wherein the said monoclonal antibody or its antigen-binding fragment are selected from Fab, Fab', F(ab')2, Fd, Fv, dAb, CDRs, single chain antibodies (e.g. scFv), humanized antibodies, chimeric antibodies, or bispecific antibodies.

In certain embodiments, the said monoclonal antibody or its antigen-binding fragment thereof, wherein the said monoclonal antibody binds to PD1 protein with $K_D$ less than approximately $10^{-5}$ M, for example, less than approximately $10^{-6}$ M, $10^{-7}$ M, $10^{-8}$ M, $10^{-9}$ M, $10^{-10}$ M, or less; preferably, detected by Fortebio molecular interaction equipment.

In certain embodiments, the said monoclonal antibody or its antigen-binding fragment thereof, wherein the said monoclonal antibody binds to PD1 protein with $EC_{50}$ less than approximately 100 nM, for example, less than 10 nM, 1 nM, 0.9 nM, 0.8 nM, 0.7 nM, 0.6 nM, 0.5 nM, 0.4 nM, 0.3 nM, 0.2 nM, 0.1 nM or less. Specifically, the said $EC_{50}$ is determined by an indirect ELISA.

In certain embodiments, the said monoclonal antibody or its antigen-binding fragment thereof, wherein the said monoclonal antibody binds to PD1 protein with $K_D$ less than approximately $10^{-5}$ M, such as less than approximately $10^{-6}$ M, $10^{-7}$ M, $10^{-8}$ M, $10^{-9}$ M, $10^{-10}$ M, or less, In certain embodiments, the said monoclonal antibody or its antigen-binding fragment thereof, wherein the said monoclonal antibody contains non-CDR regions from species other than mouse, for example, from human.

In certain embodiments, the said monoclonal antibody or its antigen-binding fragments thereof, wherein the said monoclonal antibody is produced by the hybridoma cell line LT003, and the said hybridoma cell line LT003 is preserved in China Center for Type Culture Collection (CCTCC) with the CCTCC Deposit Accession NO: C2015105.

The present invention relates to an isolated nucleic acid molecule comprising a nucleotide sequence capable of encoding $V_H$ of the antibody, wherein, the $V_H$ of the said antibody comprises: CDRs with the amino acid sequences from SEQ ID NO:9-11;

Specifically, the heavy chain of the said antibody has the amino acid sequences from SEQ ID NO:2 and SEQ ID NO:6;

More specifically, the said nucleic acid molecule has the nucleotide sequences from SEQ ID NO:1 or SEQ ID NO:5.

The present invention relates to an isolated nucleic acid molecule comprising a nucleotide sequence capable of encoding $V_L$ of the antibody, wherein, the $V_L$ of the antibody comprises CDRs with the amino acid sequences from SEQ ID NO:12-14;

Specifically, the $V_L$ of the said antibody has the amino acid sequences from SEQ ID NO:4 or SEQ ID NO:8;

More specifically, the said nucleic acid molecule has the nucleotide sequences from SEQ ID NO:3 or SEQ ID NO:7.

The present invention relates to a vector comprising the isolated nucleic acid molecule described in the present invention.

The present invention relates to a host cell comprising the isolated nucleic acid molecule described in the present invention, or vector described in the present invention.

The present invention relates to a method for preparing the monoclonal antibody or its antigen-binding fragments thereof described in the present invention, by culturing the host cell in the present invention under appropriate conditions, and recovering the said monoclonal antibody or its antigen-binding fragments thereof from the cell culture.

The present invention relates to the hybridoma cell line LT003 that is preserved in the China Center for Typical Culture Collection (CCTCC) with the CCTCC Deposit Accession NO: C2015105.

The present invention relates to a conjugate that consist of monoclonal antibody or its antigen binding fragments and conjugating part, wherein, the said monoclonal antibody is monoclonal antibody or its antigen binding fragments described in the present invention, and the said conjugating part as a detectable marker. Specifically, the said conjugating part are radioactive isotopes, fluorescein, luminescent materials, colorful substances, or enzymes.

The present invention relates to reagent kits, consisting of the monoclonal antibody or its antigen binding fragments, or the conjugates thereof described in the invention;

Specifically, the reagent kits may contain a secondary antibody, which specifically recognizes the said monoclonal antibody or its antigen binding fragments; optionally, the said secondary antibody may contain detectable markers, such as radioactive isotopes, fluorescein, luminescent materials, colorful substances, or enzymes.

The present invention relates to use of the said monoclonal antibody or its antigen binding fragments, or the conjugates thereof described in the invention in preparation of reagent kits, the said reagent kits are used in detection of the existence or the level of PD1 in samples.

The present invention relates to a pharmaceutical composition comprising the said monoclonal antibody or its antigen binding fragments, or the conjugates thereof described in the invention. Optionally, it may also comprise a pharmaceutically acceptable carrier or excipient.

The present invention relates to use of the said monoclonal antibody or its antigen binding fragments or the conjugates thereof described in the invention in preparing drugs for prevention and/or treatment and/or adjuvant treatment and/or diagnosis of tumors or anemia; specifically, the said tumors may be melanoma, renal cancer, prostate cancer, bladder cancer, colorectal cancer, gastrointestinal cancer, liver cancer, non-small cell lung cancer, ovarian cancer and leukemia.

The present inventors have found through animal experiments that, 14C12H1L1 can effectively inhibit the growth of MC38 tumor cells inoculated at right side subcutaneously in PD-1 HuGEMM mice, which the antibody drug 14C12H1L1 can significantly inhibit the tumor growth in PD-1 HuGEMM tumor-bearing mice, having an efficacy equivalent to the marketed monoclonal antibody drug Nivolumab that is approved drug targeting the same target.

The present invention relates to use of the monoclonal antibody or its antigen-binding fragments or the conjugates thereof described in the present invention for preparation drugs with the following purposes:
Blocking the binding of PD1 to PD1 ligand,
Regulating (e.g. Down-regulating) PD1 activity or level,
Relieving the immunosuppression of PD1, or
Up-regulating IFN-γ and/or IL-2 expressions in T lymphocytes;
Specifically, the said PD1 ligand is PDL1 or PDL2, preferably PDL1.

The present invention relates to an in vivo or in vitro method to apply to cells or subjects in need with an effective dose of the monoclonal antibody or its antigen-binding fragments or the conjugates thereof described in the present invention, and the said method is selected from the following:
Methods to block the binding of PD1 to PD1 ligand,
Methods to regulate (e.g. down-regulate) PD1 activity or level,
Methods to relieve the immunosuppression of PD1, or
Methods to up-regulate IFN-γ and/or IL-2 expressions in T lymphocytes;
Specifically, the said PD1 ligand is PDL1 or PDL2, preferably PDL1.

In a specific example of the present invention, the said in vitro method is intended for non-therapeutic or -diagnostic purposes.

Interferon γ (IFNγ), is mainly naturally produced by natural killer (NK) cells and natural killer T (NKT) cells, or produced by effector T cells consisting of CD4 Th1 cells and CD8 cytotoxic T lymphocytes after being stimulated by specific antigens. As an important cytokine of innate and acquired immune, IFNγ plays an import role in antagonizing or inhibiting viral, some bacterial and protozoon infections. In the meantime, IFNγ can activate macrophages and induce the expression of type 2 major histocompatibility complex (MHC) to activate immune responses to control the progression of tumors (Schoenborn J R, Wilson C B. Regulation of Interferon-7 During Innate and Adaptive Immune Responses. Advances in Immunology 2007; 96:41-101). In the in vitro study of the present invention, the anti-PD1 antibody can induce the secretion of IFNγ to activate immune responses.

Interleukin 2 (IL-2) produced by T cells is a growth factor regulating T cell subsets and a crucial factor regulating immune responses, promoting activated B cells proliferation, and participating in antibody responses, hematopoiesis and oncological surveillance. Recombinant human IL-2 has been approved by the U. S. FDA for the treatment of malignant tumors (including melanoma, renal tumor, etc.) while undergoing clinical studies for the treatment of chronic viral infections (Chavez, A. R., et al., Pharmacologic administration of interleukin-2. Ann N Y Acad Sci, 2009.1182: p. 14-27). In vitro studies, the anti-PD1 antibody of the present invention can specifically relieve the immunosuppression of PD1, activate T cells and induce IL-2 production, displaying promising prospects of extensive applications in gene therapies for neoplastic and parasitic diseases.

The monoclonal antibody or its antigen-binding fragments or the conjugates thereof described in the present invention is used for the prevention and/or treatment and/or adjuvant treatment and/or diagnosis of tumors or anemia; specifically, the said tumors may be melanoma, renal cancer, prostate cancer, bladder cancer, colorectal cancer, gastrointestinal cancer, liver cancer, non-small cell lung cancer, ovarian cancer or leukemia.

The monoclonal antibody or its antigen-binding fragments or the conjugates thereof described in the present invention is used to:
Block the binding of PD1 to PD1 ligand,
Regulate (e.g. down-regulate) PD1 activity or level,
Relieve the immunosuppression of PD1, or
Up-regulate IFN-γ and/or IL-2 expressions in T lymphocytes;
Specifically, the said PD1 ligand is PDL1 or PDL2, preferably PDL1.

In a specific example of the present invention, the monoclonal antibody or its antigen-binding fragments or the conjugates thereof described in the present invention only blocks the binding of PD1 to PDL1.

The present invention relates to a method for the prevention and/or treatment and/or adjuvant treatment and/or diagnosis of tumors or anemia, including the procedure to apply to subjects with an effective dose of the monoclonal antibody or its antigen-binding fragments or the conjugates thereof described in the present invention; specifically, the said tumors may be melanoma, renal cancer, prostate cancer, bladder cancer, colorectal cancer, gastrointestinal cancer, liver cancer, non-small cell lung cancer, ovarian cancer or leukemia.

Unless otherwise defined herein, scientific and technical terms used in connection with the present invention shall have the meanings that are commonly understood by those of ordinary skill in the art. Furthermore, laboratory techniques of cell and tissue culture, molecular genetics, oligo- or polynucleotide chemistry, and immunology described herein are those well-known and commonly used in the art. Meanwhile, to better understand the present invention, the following terms, unless otherwise indicated, shall be understood to have the following meanings:

As used in this invention, the term "Amino acid sequence of PD1 protein (Programmed cell death protein 1, NCBI GenBank: NP_005009.2)" comprises the full length PD1 protein, or PD1ECD (extracellular segment of PD1) or PD1ECD-containing fragments; and also comprises the fusion protein of PD1ECD, for example, fused with the Fc protein fragments of mouse or human IgG (mFc or hFc). Furthermore, understood by those of ordinary skill in the art, the amino acid sequence of PD1 protein can have naturally or artificial mutations (including but not limited to substitutions, deletions, and/or additions), not affecting its biological functions. Therefore, in the present invention, the term "PD1 protein" should include all such sequences and their natural or artificial variants. Furthermore, when describing the sequence fragments of PD1 protein, the said sequence fragments comprise both the sequence fragments and the corresponding sequence fragments in its natural or artificial variants.

As used in this invention, the term "Amino acid sequence of PDL1 protein (Programmed death-ligand 1, NCBI Genebank ID: NP_054862.1)" comprises the full length PDL1 protein, or PDL1ECD (extracellular segment of PDL1) or PDL1ECD-containing fragments; and also comprises the fusion protein of PDL1ECD, for example, fused with the Fc protein fragments of mouse or human IgG (mFc or hFc). Furthermore, understood by those of ordinary skill in the art, the amino acid sequence of PDL1 protein can have naturally or artificial mutations (including but not limited to substitutions, deletions, and/or additions), not affecting its biological functions. Therefore, in the present invention, the term "PDL1 protein" should include all such sequences and their natural or artificial variants. Furthermore, when describing the sequence fragments of PDL1 protein, the said sequence fragments comprise both the sequence fragments and the corresponding sequence fragments in its natural or artificial variants.

As used in this invention, the term "$EC_{50}$" refers to the concentration for 50% of maximal effect.

As used in this invention, the term "antibody" refers to immunoglobulin proteins, which typically composed of two pairs of polypeptide chains (each pair has a "light" (L) chain and a "heavy" (H) chain). The light chains are classified as κ and λ light chains. The heavy chains are classified as μ, δ, γ, α, or ε, and respectively, define isotype antibodies as IgM, IgD, IgG, IgA and IgE. In light chains and heavy chains, variable regions and constant regions are connected by a "J" region consisting of about 12 or more amino acids. The heavy chain also contains a "D" region with about 3 or more amino acids. Each heavy chain contains a variable region ($V_H$) and a constant region ($C_H$), which consists of 3 domains ($C_H1$, $C_H2$, and $C_H3$). Each light chain contains a variable region ($V_L$) and a constant region ($C_L$), which consists of one domain $C_L$. The constant region can mediate the binding of immune globulin to host tissues or factors, including various cells in the immune system (e.g., effector cells) and the complement component 1q (C1q) of the classical complement system. $V_H$ and $V_L$ can also be subdivided into regions with high variability (called complementarity determining region (CDR)), which are separated by relatively conservative regions called framework regions (FR). From the amino terminus to the carboxyl terminus, each $V_H$ and $V_L$ is composed of 3 CDRs and 4 FRs, in the order of FR1, CDR1, FR2, CDR2, FR3, CDR3, and FR4. The variable regions ($V_H$ and $V_L$) of the heavy chain and light chain form the antibody binding site. Distribution of amino acids to the regions or domains follow the definitions by Kabat in Sequences of Proteins of Immunological Interest (National Institutes of Health Bethesda, MD (1987 and 1991)), or Chothia & Lesk (1987) Mol. Biol., 196:901-917; or Chothia et al. (1989) Nature, 342:878-883. The term "antibody" is not restricted by any particular method of producing them. For example, it includes, in particular, recombinant antibodies, monoclonal antibodies, and polyclonal antibodies. Antibodies can be different isotypes, for example, IgG (such as IgG1, IgG2, IgG3, or IgG4 subtype), IgA1, IgA2, IgD, IgE, or IgM antibodies.

As used in this invention, the term "antigen binding fragments" refers to a polypeptide containing fragments of a full-length antibody, maintaining the ability to bind specifically to the same antigen, and/or to compete with the full length antibody to bind to the antigen, which is also called "the antigen binding portion". See Fundamental Immunology, Ch. 7 (Paul, W., ed. 2, Raven Press, N. Y. (1989)), including the entire article and references in this invention for all purposes. Antigen binding fragments can be generated by recombinant DNA techniques or by cleaving intact antibodies with proteolytic enzymes or chemicals. In some cases, the antigen binding fragments include Fab, Fab', F(ab')$_2$, Fd, Fv, dAb, and CDR fragments, single chain antibodies (e.g., scFv), chimeric antibodies, diabody, and the polypeptides that at least contains an antibody portion which is sufficient to confer a specific antigen binding capacity to the polypeptides.

In some cases, the antigen binding fragment is a diabody, namely, a dimeric antibody fragment, whose $V_H$ and $V_L$ domains are expressed on a single polypeptide chain, however, because of using a too short linker the to allow pairing between the two domains of the same chain, the domains are forced to pair with complementary domains on another chain to generate two antigen binding sites (see, for example, Holliger P. et al., Proc. Natl. Acad. Sci. USA 90: 6444-6448 (1993), and Poljak R. J. et al., Structure 2: 1121-1123 (1994)).

Using conventional techniques known by those of ordinary skill in the art (such as recombinant DNA technology or enzymatic/chemical cleavage), an antigen binding fragment (such as the above described antibody fragments) may be obtained from a given antibody (e.g. monoclonal antibodies 14C12, 14C12H1L1 provided herein in the invention), and screened for specificity in the same manner as for the full antibody.

In this invention, unless specified otherwise, the term "antibody" refers to not only the intact antibody, but also the antigen binding fragments of the antibody.

As used in this invention, the terms "mAb" and "monoclonal antibodies" refers to an antibody or a fragment of an antibody that is derived from a group of highly homologous antibodies, i.e. from a group of identical antibody molecules, except for mutations that may arise spontaneously. Monoclonal antibody has high specificity against a single epitope on the antigen. Polyclonal antibodies are different from monoclonal antibodies, containing at least 2 or more different antibodies, which usually recognize different epitopes on the antigen. Monoclonal antibodies can be obtained with hybridoma technology reported originally by Kohler et al., (Nature, 256: 495, (1975)), as well as recombinant DNA Technology (see U.S. Pat. No. 4,816,567).

As used in this invention, the term "humanized antibody" refers to an antibody or its fragments, derived from a human immunoglobulin (receptor antibody), whose CDRs or part of CDRs are replaced by the CDR regions of a non-human antibody (donor antibody), where the donor antibody may be a non-human antibody (for example, mice, rats, or rabbits) with predictive specificity, binding affinity, or reactivity. In addition, some amino acid residues of the receptor antibody framework region (FR) can also be replaced by the corresponding amino acid residues of the non-human source, or replaced by the amino acid residues of other antibodies to further improve or optimize the performance of the antibody. For more details on humanized antibodies, see for example Jones, et al., Nature, 321: 522-525 (1986); Reichmann et al., Nature, 332: 323-329 (1988); Presta, Curr. Op. Struct. Biol., 2: 593-596 (1992); and Clark, Immunol. Today, 21: 397-402 (2000).

As used in this invention, the term "isolate" or "isolated" means obtained by artificial means in the natural state. If there is a certain kind of "isolated" matter or component in nature, it may be due to the change in its natural environment, or isolated from the natural environment, or both. For example, polynucleotide or polypeptide in a natural existence in a living animal will be called "isolated" if it was separated with high purity in the same natural state. The term "isolate" or "isolated" does not exclude existence of artificial or synthetic material, or other impurities that does not affect the activity.

As used in this invention, the term "vector" refers to a nucleic acid delivery vehicle that can be inserted with polynucleotide. The vector that can have the protein that is encoded by the inserted polynucleotide expressed is called an expression vector. Vectors can be inserted into the host cell by transformation, transduction, or transfection, so the genetic substances carried by the vector can be expressed in the host cell. Vectors are well known to the technical personnel in the field, including but not limited to: plasmid; phasmid; cosmid; artificial chromosome such as yeast artificial chromosome (YAC), bacterial artificial chromosome (BAC), or P1 derived artificial chromosome (PAC); phage such as λ phage or M13 phage and animal viruses etc. Animal viruses may include but not limited to, reverse transcriptase virus (including lentivirus), adenovirus, adeno-associated virus, herpes virus (e. g. herpes simplex virus), chicken pox virus, baculovirus, papilloma virus, and papova virus (such as SV40). A vector can contain multiple components that control expression, including but not limited to, promoter, transcription initiation factor, enhancer, selection element, and reporter gene. In addition, the vector may also contain replication initiation site.

As used in this invention, the term "host cell" refers to cells that can import vectors, including but not limited to, prokaryotic cells such as *E. coli* and *Bacillus subtilis*, fungal cells such as yeast and *Aspergillus*, insect cells such as S2 *Drosophila* cells and Sf9, or animal cells such as fibroblast cells, CHO cells, COS cells, NSO cells, HeLa cells, BHK cells, HEK293 cells or human cells.

As used in this invention, the term "specific binding" refers to a non-random binding between two molecules, such as the interaction between the antibody and its target antigen. In some embodiments, a specific binding of an antibody to an antigen means an affinity ($K_D$), for example less than about $10^{-5}$ M, in particular, less than $10^{-6}$ M, $10^{-7}$ M, $10^{-8}$ M, $10^{-9}$ M, $10^{-10}$ M, or less.

As used in this invention, the term "$K_D$" refers to the dissociation equilibrium constant of specific interaction between antibody and antigen, to describe the binding affinity between antibodies and antigens. The smaller the equilibrium dissociation constant is, the tighter the antibody binds antigen, the higher the affinity between the antibody and the antigen is. Typically, antibodies (e.g., monoclonal antibodies 14C12, 14C12H1L1 in the present invention) bind to antigens (e.g., PD1 protein) with a $K_D$ less than approximately $10^{-5}$ M, for example, less than $10^{-6}$ M, $10^{-7}$ M, $10^{-8}$ M, $10^{-9}$ M or $10^{-10}$ M or even less. $K_D$ can be measured by any method well known to the technical personnel in the field, for example, using Fortebio Octet System As used in this invention, the terms "monoclonal antibody" and "mAb" have the same meaning and are used interchangeably; the terms "polyclonal antibody" and "PcAb" have the same meaning and are used interchangeably; the terms "polypeptide" and "protein" have the same meaning and are used interchangeably. Also in the present invention, amino acids are usually represented by single letter or three letter abbreviations known to this field. For example, Alanine can be represented as A or Ala.

As used in this invention, the terms "hybridoma" and "hybridoma cell line" can be used interchangeably, and when mentioned herein, include the subclone and progeny cells of hybridoma. For example, when mentioned herein, hybridoma cell line LT003 also includes the subclone and progeny cells of LT003.

As used in this invention, the term "pharmaceutically acceptable carrier or excipient" refers to a carrier and/or an excipient pharmaceutically and/or physiologically compatible with subjects and active ingredients, and widely recognized in the field herein (Remington's Pharmaceutical Sciences. Edited by Gennaro A R, 19th ed. Pennsylvania: Mack Publishing Company, 1995), including but not limited to: pH adjustors, surfactants, adjuvants, and ionic strength enhancers. For example, pH adjustors include but not limited to phosphate buffer solution; surfactants include but not limited to cationic, anionic or nonionic surfactants such as Tween-80; ionic strength enhancers include but not limited to sodium chloride.

As used in this invention, the term "effective dose" is defined as an amount of a therapeutic sufficient to achieve or at least partially achieve the desired effect. For example, effective prevention dose (e.g. for cancer) is the amount to prevent, stop, or delay the occurrence of diseases (e.g. cancer); effective treatment dose is the amount to cure, or at least partially stop, the disease and its complications in patients with the disease. Determination of such an effective dose is entirely within the scope of the capabilities of the technical personnel in the field. For example, the effective treatment dose will depend on the severity of the disease, the overall state of the patient's immune system, the general background of patients such as age, weight and gender, administration method of the said drug, and other concomitant treatments, etc.

Effects of the Invention

The monoclonal antibodies in the present invention, especially 14C12H1L1, is capable of binding to PD1 specifically, effectively blocking the binding of PD1 to PDL1, and relieving the immunosuppression of PD1 to activate T lymphocytes. Wherein, the PD1 antibody 14C12H1L1 can induce the secretions of IFN-γ and IL-2 much better than the control antibody 5C4 (5C4: PD1 antibody from Medarex Inc.: Alan J. Korman, et al., Human monoclonal antibodies to programmed death 1 (PD1) and methods for treating cancer using anti-PD1 antibodies alone or in combination with other immunotherapeutics, U.S. Pat. No. 8,008,449 B2). The monoclonal antibodies of the present invention, especially 14C12H1L1, have an antitumor effect equivalent to the approved drug Nivolumab for the same target. The antibodies of the present invention have the potential to become or to be prepared into drugs for the prevention and/or treatment of non-small cell lung cancer, renal cell carcinoma, ovarian cancer, melanoma, leukemia or anemia.

Figure 1:
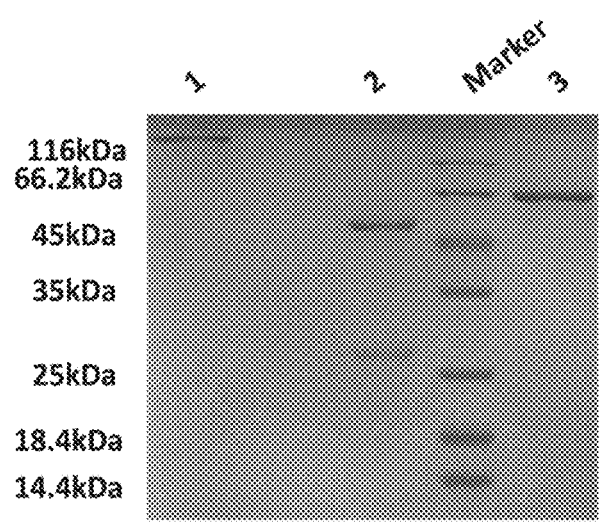
FIG. 1: SDS-PAGE Results of Humanized Monoclonal Antibody 14C12H1L1. From left to right: 1. 1 μg antibody in non-reduced loading buffer; 2. 1 μg antibody in reduced loading buffer; 5 μL Marker; 3. 1 μg BSA.

Hybridoma cell line LT003, has been preserved in the China Center for Typical Culture Collection (CCTCC) in Wuhan University, Wuhan, China 430072 on Jun. 16, 2015 with CCTCC Deposit Accession NO: C2015105

DETAILED DESCRIPTION OF THE INVENTION

The invention will now be described in detail. As will be appreciated by one skilled in the art, the following examples are only used for the description of the invention, and not to be deemed to limit the scope of the invention. The cases without the specific descriptions of techniques or conditions were carried out in accordance with the literature in the field (e.g., Guide to Molecular Cloning, written by J Sambrook, et al, translated by Peitang Huang, et al, third Edition, Science Press) or in accordance with the product instruction manual. The reagents or instruments with no specified manufacturer were all conventional products available commercially.

In the examples below, T cells used were from Akeso Biopharma, Inc.; the BALB/C mice were purchased from Guangdong Medical Laboratory Animal Center. The PD-1 HuGEMM mice used were from Nanjing Galaxy Biopharma Co., Ltd.; MC38 cells were from Shanghai Fudan IBS Cell Center; the marketed drug for the same target, Nivolumab (Opdivo®) used was from Bristol-Myers Squibb Company.

Example 1: Acquisition of Hybridoma Cell Line LT003 and Preparation of Monoclonal Antibody 14C12

1. Establishment of Hybridoma Cell Line LT003

Used PD1-mFc (PD1: Programmed cell death protein 1, NCBI GenBank ID:NP_005009.2) fusion protein as the antigen, and fused the splenocytes of immunized BALB/C mice (purchased from Guangdong Medical Laboratory Animal Center) and mouse myeloma cells into hybridoma cells by currently established method (for example, Stewart, S. J., "Monoclonal Antibody Production", in Basic Methods in antibody Production and Characterization, Eds. G. C. Howard and D. R. Bethell, Boca Raton: CRC Press, 2000).

Coating the microplate with PD1-mFc as the antigen, and the hybridoma cells were screened by indirect ELISA to obtain hybridoma cells that secrets new antibodies specifically binding to PD1.

Screened out the hybridoma cell lines capable of secreting monoclonal antibodies binding to PD1 by competition ELISA against the ligand PDL1-hFc fused protein (PDL1: Programmed death-ligand 1, NCBI Genebank ID:NP_054862.1), and obtained stable hybridoma cell lines by limited dilution method, and then obtained stable LT003 cell lines by limited dilution method (the monoclonal antibody secreted from LT003 is named 14C12).

Hybridoma cell line LT003 (PD1-14C12), has been preserved in the China Center for Typical Culture Collection (CCTCC) in Wuhan University, Wuhan, China 430072 on Jun. 16, 2015 with CCTCC Deposit Accession NO: C2015105.

2. Preparation of Monoclonal Antibody 14C12

LT003 cell line in the present invention was cultured using IMDM medium containing 10% low IgG fetal bovine serum for 7 days, and then the cell culture supernatant was harvested and purified to get the antibody 14C12.

Example 2: Acquisition of Light-Chain and Heavy-Chain Sequences of Monoclonal Antibody 14C12

Extracted mRNA from the hybridoma cell line LT003 prepared in Example 1 above according to the manual of the cell/bacterial total RNA extraction reagent kit (Tiangen, Product No DP430).

Synthesized cDNA according to the manual of Invitrogen SuperScript® III First-Strand Synthesis System for RT-PCR Kit and carried out PCR amplification.

Directly carried out TA cloning using the PCR amplification products according to the instructions of pEASY-T1 Cloning Kit (Transgen CT101).

Sequenced the TA cloning products, and obtained the following results:

```
DNA sequencing results of V_H: (354 bp)
                                    (SEQ ID NO: 1)
GAGGTCAAACTGGTGGAGAGCGGCGGCGGGCTGGTGAAGCCCGGCGGG

TCACTGAAACTGAGCTGCGCCGCTTCCGGCTTCGCCTTTAGCTCCTAC

GACATGTCATGGGTGAGGCAGACCCCTGAGAAGCGCCTGGAATGGGTC

GCTACTATCAGCGGAGGCGGGCGATACACCTACTATCCTGACTCTGTC

AAAGGGAGATTCACAATTAGTCGGGATAACGCCAGAAATACTCTGTAT

CTGCAGATGTCTAGTCTGCGGTCCGAGGATACAGCTCTGTACTATTGT

GCAAACCGGTACGGCGAAGCATGGTTTGCCTATTGGGGACAGGGCACC

CTGGTGACAGTCTCTGCC

Encoded protein sequence: (118 aa)
                                    (SEQ ID NO: 2)
EVKLVESGGGLVKPGGSLKLSCAASGFAFSSYDMSWVRQTPEKRLEWV

ATISGGGRYTYYPDSVKGRFTISRDNARNTLYLQMSSLRSEDTALYYC

ANRYGEAWFAYWGQGTLVTVSA

DNA sequencing results of V_L: (318 bp)
                                    (SEQ ID NO: 3)
GACATTAAGATGACACAGTCCCCTTCCTCAATGTACGCTAGCCTGGGC

GAGCGAGTGACCTTCACATGCAAAGCATCCCAGGACATCAACACATAC

CTGTCTTGGTTTCAGCAGAAGCCAGGCAAAAGCCCCAAGACCCTGATC

TACCGGGCCAATAGACTGGTGGACGGGGTCCCCAGCAGATTCTCCGGA

TCTGGCAGTGGGCAGGATTACTCCCTGACCATCAGCTCCCTGGAGTAT

GAAGACATGGGCATCTACTATTGCCTGCAGTATGATGAGTTCCCTCTG

ACCTTTGGAGCAGGCACAAAACTGGAACTG

Encoded protein sequence: (106 aa)
                                    (SEQ ID NO: 4)
DIKMTQSPSSMYASLGERVTFTCKASQDINTYLSWFQQKPGKSPKTLI

YRANRLVDGVPSRFSGSGSGQDYSLTISSLEYEDMGIYYCLQYDEFPL

TFGAGTKLEL
```

2. Preparation of Recombinant Monoclonal Antibody 14C12 (Re)

Separately cloned the heavy-chain cDNA sequence (the variable region sequence is SEQ ID NO:1) and the light-chain cDNA sequence (the variable region sequence is SEQ ID NO:3) of 14C12 (Re) into the pUC57simple (provided by GenScript Biotech Corp.) vector (enzymatic cleavage sites: XbaI & BamHI), and obtained pUC57simple-14C12H and pUC57simple-14C12L plasmids, respectively.

Enzymatically cleaved (HindIII & EcoRI) the plasmids pUC57simple-14C12H and pUC57simple-14C12L, respectively, and then sub-cloned the heavy and light chains recovered from electrophoresis into the pcDNA3.1 vector, extracted both recombinant plasmids and co-transfect 293F cells.

After 7 days cell culture, the cell culture supernatant was centrifuged by high-speed centrifugation and filtered by vacuum filtration with microporous membrane and loaded onto the HiTrap MabSelectSuRe column, and then the antibody was eluted with Elution Buffer in one step, and then went through HiTrap Desalting column, and recovered into PBS buffer, and then the recombinant antibody 14C12 (Re) was obtained after further purification.

As validated by ELISA binding activity assay, the recombinant antibody 14C12 (Re) had a binding activity equivalent to the antibody 14C12, and hence can be further used in the subsequent antibody humanization design.

Example 3: Design of Heavy-Chain and Light-Chain Sequences of Humanized Antibody 14C12H1L1

1. Design of Light-Chain and Heavy-Chain Sequences of Humanized Antibody 14C12H1L1

According to the three-dimensional crystal structure of PD1 protein (Shinohara T, et al., Structure and chromosomal localization of the human PD1 gene (PDCD1). Genomics 1995, 23 (3):704-6)) and the sequences of the antibody 14C12 obtained in Example 2, through computer antibody modeling, amino acids mutation was designed according to the model, and obtained the variable region sequences of the antibody 14C12H1L1 (Heavy chain constant region is Ig gamma-1 chain C region, ACCESSION:P01857 (SEQ ID NO: 15); light chain constant region is Ig kappa chain C region, ACCESSION:P01834 (SEQ ID NO: 16)), as follows:

```
DNA sequence of heavy chain variable region:
(354 bp)
                                   (SEQ ID NO: 5)
GAAGTGCAGCTGGTCGAGTCTGGGGGAGGGCTGGTGCAGCCCGGCGGG

TCACTGCGACTGAGCTGCGCAGCTTCCGGATTCGCCTTTAGCTCCTAC

GACATGTCCTGGGTGCGACAGGCACCAGGAAAGGGACTGGATTGGGTC

GCTACTATCTCAGGAGGCGGGAGATACACCTACTATCCTGACAGCGTC

AAGGGCCGGTTCACAATCTCTAGAGATAACAGTAAGAACAATCTGTAT

CTGCAGATGAACAGCCTGAGGGCTGAGGACACCGCACTGTACTATTGT

GCCAACCGCTACGGGGAAGCATGGTTTGCCTATTGGGGGCAGGGAACC

CTGGTGACAGTCTCTAGT

Encoded protein sequence: (118 aa)
                                   (SEQ ID NO: 6)
EVQLVESGGGLVQPGGSLRLSCAASGFAFSSYDMSWVRQAPGKGLDWV

ATISGGGRYTYYPDSVKGRFTISRDNSKNNLYLQMNSLRAEDTALYYC

ANRYGEAWFAYWGQGTLVTVSS

DNA sequence of light chain variable region:
(321 bp)
                                   (SEQ ID NO: 7)
GACATTCAGATGACTCAGAGCCCCTCCTCCATGTCCGCCTCTGTGGGC

GACAGGGTCACCTTCACATGCCGCGCTAGTCAGGATATCAACACCTAC

CTGAGCTGGTTTCAGCAGAAGCCAGGGAAAAGCCCCAAGACACTGATC

TACCGGGCTAATAGACTGGTGTCTGGAGTCCCAAGTCGGTTCAGTGGC

TCAGGGAGCGGACAGGACTACACTCTGACCATCAGCTCCCTGCAGCCT

GAGGACATGGCAACCTACTATTGCCTGCAGTATGATGAGTTCCCACTG

ACCTTTGGCGCCGGGACAAAACTGGAGCTGAAG

Encoded protein sequence: (107 aa)
                                   (SEQ ID NO: 8)
DIQMTQSPSSMSASVGDRVTFTCRASQDINTYLSWFQQKPGKSPKTLI

YRANRLVSGVPSRFSGSGSGQDYTLTISSLQPEDMATYYCLQYDEFPL

TFGAGTKLELK
```

Example 4: Preparation and SDS-PAGE Electrophoresis of Humanized Monoclonal Antibody 14C12H1L1

Separately cloned the heavy-chain cDNA (the variable region sequence is SEQ ID NO:5, heavy chain constant region is Ig gamma-1 chain C region, ACCESSION:P01857 (SEQ ID NO: 15)) and light-chain cDNA (the variable region sequence is SEQ ID NO:7, light chain constant region is Ig kappa chain C region, ACCESSION:P01834 (SEQ ID NO:16)) of 14C12H1L1 into the pUC57simple (provided by GenScript Biotech Corp.) vector (enzymatic cleavage sites: XbaI & BamHI) to obtain pUC57simple-14C12H1 and pUC57simple-14C12L1 plasmids, respectively. Sub-cloned the plasmids into pcDNA3.1 vector respectively (enzymatic cleavage sites: XbaI & BamHI), extracted both recombinant plasmids and co-transfect 293F cells.

After 7 days cell culture, the cell culture was centrifuged by high-speed centrifugation and filtered via vacuum filtration with microporous membrane and loaded onto the HiTrap MabSelectSuRe column, and then the antibody was eluted with Elution Buffer in one step, went through HiTrap Desalting column and recovered into PBS buffer, and purified further to obtain the recombinant antibody 14C12H1L1, which was analyzed by SDS-PAGE electrophoresis.

The results were shown in FIG. 1, the reduced target protein appeared at approximately 24.5 kD and 49 KD, and the non-reduced target protein appeared at approximately 147 kD.

Example 5: Kinetics Measurements of the Antibodies

The binding kinetics of the antibody 14C12 and humanized antibody 14C12H1L1 to the antigen PD1 was measured by Fortebio Octet System.
 1. Cleaved PD1-mFc protein with TEV protease, and obtained PD1 antigen by column purification.
 2. The antigen PD1 (the concentration at 1 μg/ml) labeled with biotin was immobilized on the surface of SA sensor and equilibrated in PBST buffer, and then bound antibodies 14C12, 14C12H1L1 and 5C4, and the antibodies were diluted with each dilution three-fold relative to the previous one since 200 nM. The dissociation of antigen and antibody were also in PBST.

Figure 2:
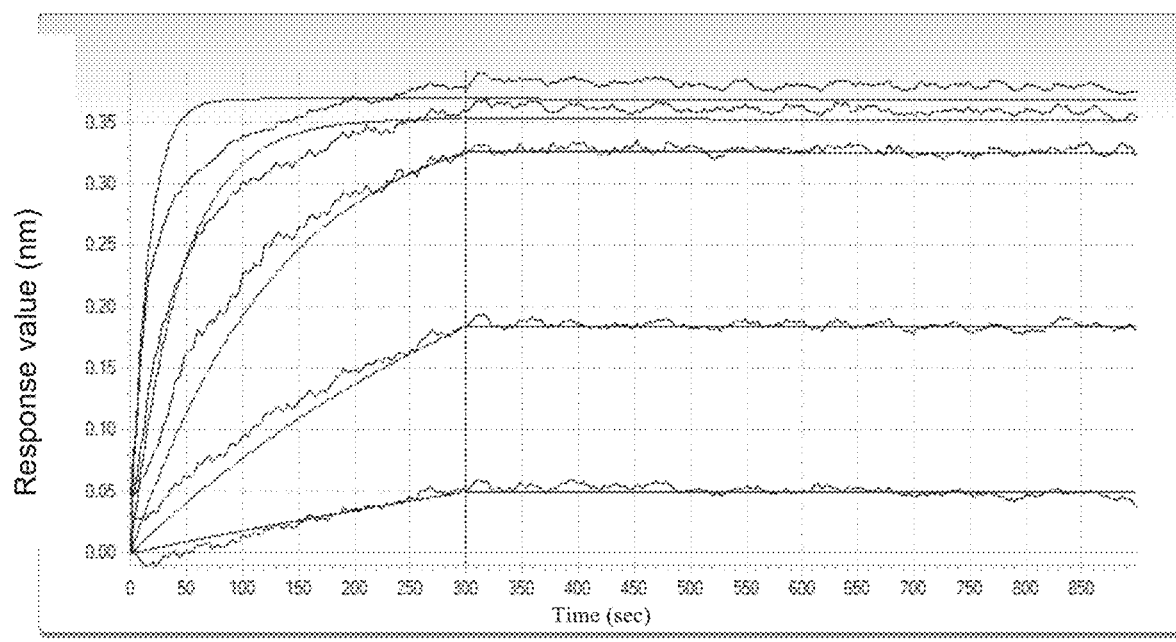
FIG. 2: Binding kinetics of Antibody 14C12.
Figure 3:
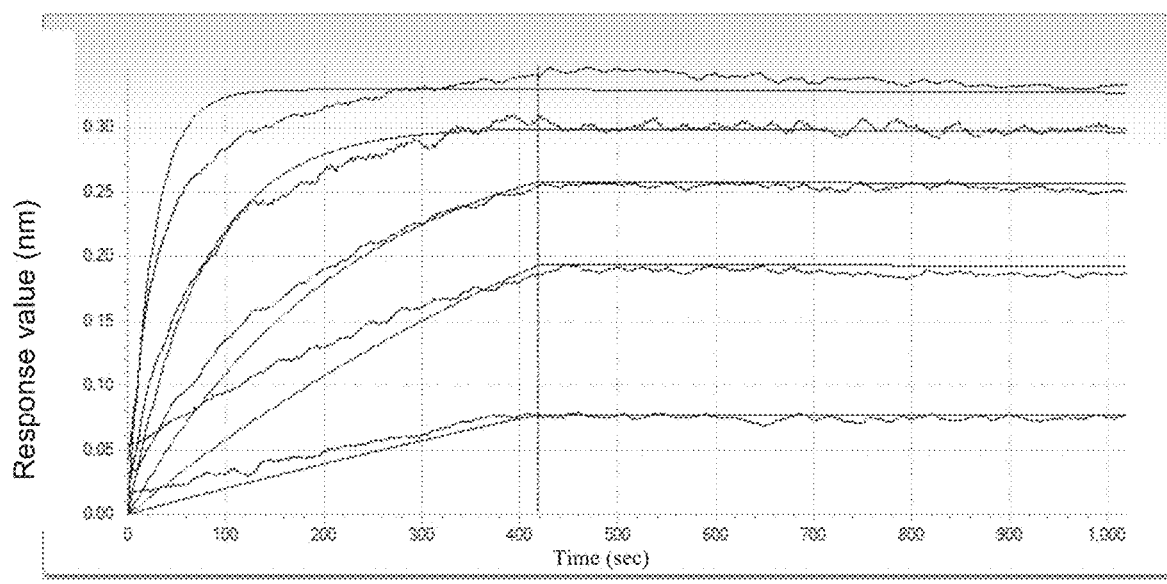
FIG. 3: Binding kinetics of Antibody 14C12H1L1.
Figure 4:
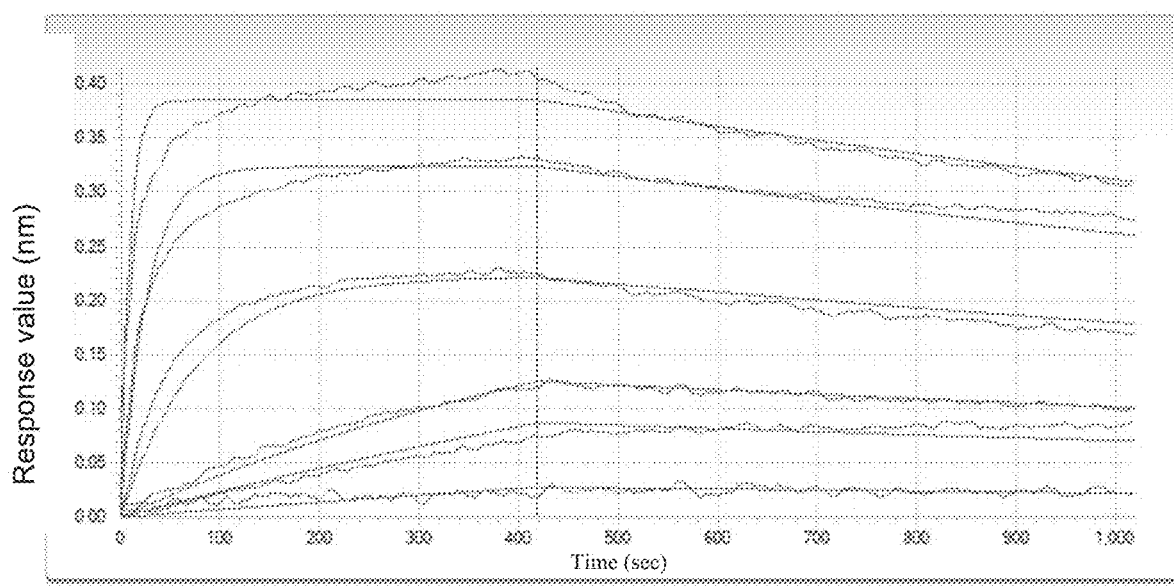
FIG. 4: Binding kinetics of Antibody 5C4.

Binding kinetics of the antibodies 14C12, 14C12H1L1 and 5C4 were shown in Table 1 and FIGS. 2, 3 and 4, respectively. The results showed that both 14C12 and 14C12H1L1 had good affinities to PD1, with a higher affinity than that of 5C4.

TABLE 1

Dynamic Parameters of Antibody 14C12.

| Antibody Name | $K_D$ (M) | Kon (1/Ms) | Ko Error | Kdis (1/s) | Kdis Error |
|---|---|---|---|---|---|
| 14C12 | 1.81E−11 | 3.38E+05 | 8.23E+03 | 6.12E−06 | 1.04E−05 |
| 14C12H1L1 | 2.42E−11 | 3.17E+05 | 5.90E+03 | 7.66E−06 | 8.70E−06 |
| 5C4 | 6.46E−10 | 5.63E+05 | 1.38E+04 | 3.63E−04 | 9.77E−06 |

$K_D$: Dissociation constant;
$K_{on}$: Binding rate of antigen and antibody;
$K_{dis}$: Dissociation rate of antigen and antibody;
$K_D$ = Kdis/Kon.

Example 6: Binding Activity of Antibody and Antigen PD1 Measured by Indirect ELISA The binding activities of antibodies 14C12H1L1 and 5C4 to PD1 were measured separately by indirect ELISA as follows:

After incubated with PD1-mFc at 4° C. overnight, the microplate was blocked with 1% BSA at 37° C. for 2h, and then the antibodies were added separately and incubated at 37° C. for 30 min, and then HRP-labeled secondary antibody (goat anti-human IgG (H+L)) (Jackson, 109-035-088) was added, and then TMB (Neogen, 308177) was added to react for 5 mins and the absorbance was read at the wavelength of 450 nm in a microplate reader.

Figure 5:
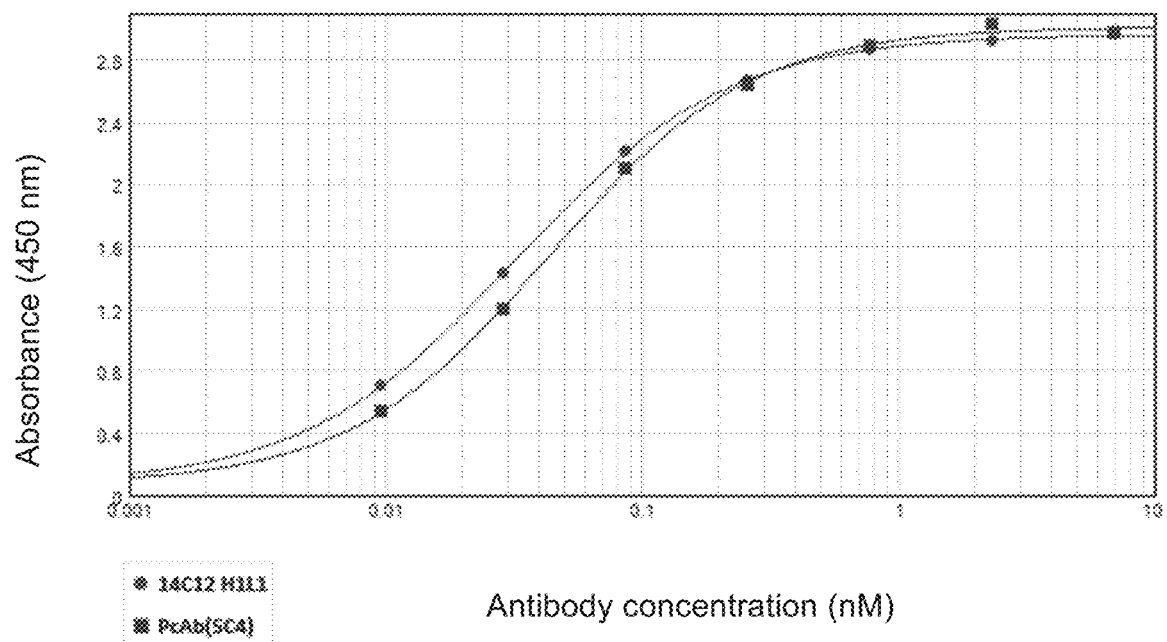
FIG. 5: ELISA results of 14C12H1L1 and 5C4 binding to PD1.

The binding results of antibodies 14C12H1L1 and 5C4 to the antigen PD1 were shown in FIG. 5. As shown in FIG. 5, both the antibodies 14C12H1L1 and 5C4 can bind to PD1 protein effectively with dose-dependency. The absorbance intensities at different doses were shown in Table 2. Through Curve Simulation using quantitative analyses of absorbance values, EC50 of 14C12H1L1 and 5C4 binding with PD1 were then determined to be 0.032 nM and 0.043 nM, respectively.

TABLE 2

Absorbance Intensities of 14C12H1L1 and 5C4 binding to PD1

| Antibody concentration (μg/mL) | 14C12H1L1 | | 5C4 | |
|---|---|---|---|---|
| 1 | 2.970 | 2.954 | 2.959 | 2.991 |
| 0.3 | 2.886 | 2.961 | 2.978 | 3.079 |
| 0.1 | 2.864 | 2.868 | 2.838 | 2.926 |
| 0.03 | 2.674 | 2.669 | 2.617 | 2.659 |
| 0.01 | 2.222 | 2.201 | 1.981 | 2.221 |
| 0.003 | 1.383 | 1.464 | 1.169 | 1.222 |
| 0.001 | 0.676 | 0.736 | 0.527 | 0.548 |
| 0 | 0.062 | 0.062 | 0.065 | 0.073 |
| Secondary Antibody | HRP-labeled secondary antibody (goat anti-human IgG) | | | |

Antigen coating: PD1-mFc (0.5 μg/mL)

Example 7: Binding Activities of Antibodies to Antigen PD1 Against PDL1 by Competition ELISA Binding activities of humanized antibody 14C12H1L1 and 5C4 to antigen PD1 against PDL1 were measured by competition ELISA as follows:

After incubated with PD1-hFc at 4° C. overnight, the microplate was blocked with 1% BSA for 2h, and antibodies 14C12H1L1 and 5C4 with different concentrations (see Table 3 for the dilute strengths) were mixed with PDL1-mFc for 10 min, and the mixtures were incubated at 37° C. for 30 min, and then corresponding anti-human and anti-mouse enzyme-labeled second antibodies respectively and incubate at 37° C. for 30 min were added. The absorbance at the wavelength of 450 nm was read in a microplate reader.

Figure 6:
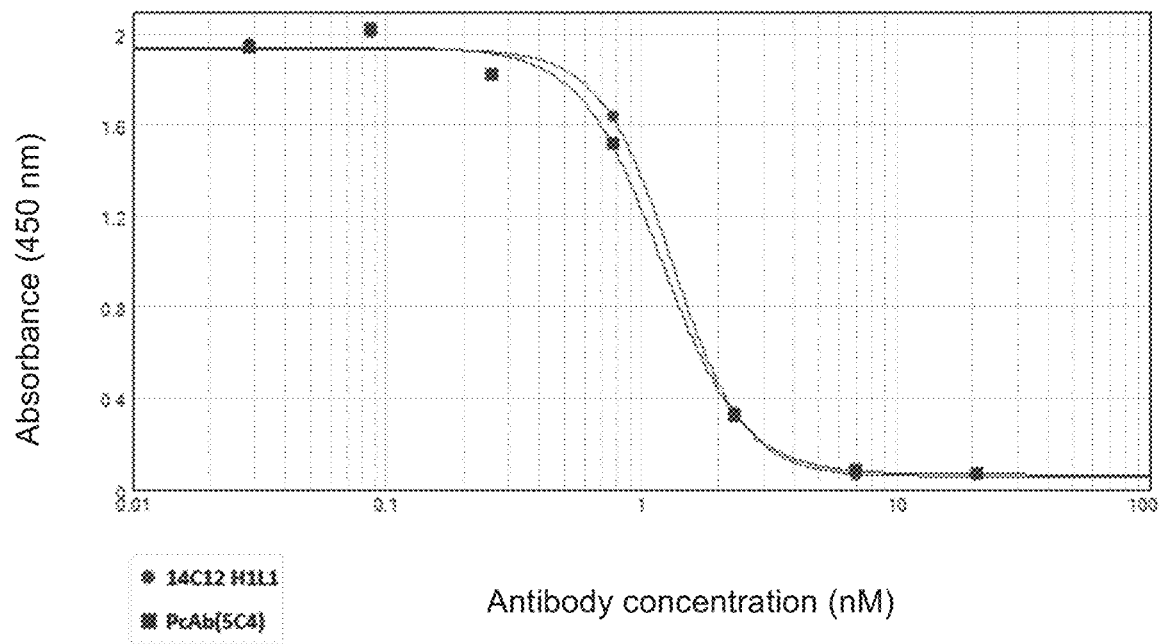
FIG. 6: Competition ELISA results of 14C12H1L1 and 5C4 binding to PD1 against PDL1.

The binding results of antibodies 14C12H1L1 and 5C4 to the antigen PD1 were shown in FIG. 6. As shown in FIG. 6, the antibody 14C12H1L1 can compete against PDL1 and bind to PD1 protein effectively with dose-dependency. The absorbance intensities at different doses were shown in Table 3. Through Curve Simulation using quantitative analyses of absorbance values, EC50 of 14C12H1L1 and 5C4 binding activity were then determined to be 1.322 nM and 1.199 nM, respectively.

TABLE 3

Competitive Binding of 14C12H1L1 and 5C4 to PD1 against PDL1

| Antibody concentration/ dilution gradient | 14C12H1L1 | | 5C4 | |
|---|---|---|---|---|
| 1.5 μg/ml | 0.062 | 0.064 | 0.070 | 0.075 |
| 1:3 | 0.069 | 0.064 | 0.081 | 0.086 |
| 1:9 | 0.363 | 0.305 | 0.372 | 0.269 |
| 1:27 | 1.727 | 1.543 | 1.429 | 1.604 |
| 1:81 | 1.892 | 1.752 | 1.766 | 1.881 |
| 1:243 | 1.984 | 2.029 | 2.045 | 2.005 |
| 1:729 | 1.937 | 1.978 | 1.934 | 1.954 |
| 0 | 1.870 | 1.977 | 1.933 | 1.977 |
| Ligand | PDL1-mFc 0.3 μg/ml | | | |
| Secondary Antibody | HRP-labeled goat anti-mouse secondary antibody | | | |

Antigen coating PD1-mFc 0.5 μg/mL

Example 8: Binding Activity of Antibodies to Cell Surface Antigen PD1 by Flow Cytometry Host cells 293T expressing PD1 antigen were constructed, and labeled with the humanized antibody 14C12H1L1 prepared in the present invention (see Example 4). The ability of the antibody 14C12H1L1 to bind specifically to cell surface antigen in its native conformation was analyzed and validated by flow cytometry.

1. Construction of Host Cell 293T Expressing PD1 Antigen

The specific steps were as follows:

Construction of the host cell 293T expressing PD1 antigen: 293T cells were transfected with the PD1-containing vector pLenti6.3-PD1 (vector pLenti6.3 was purchased from Invitrogen Corporation) according to the manual of LipofectaminTransfection Kit (purchased from Invitrogen Corporation) to obtain the stable pool of 293T-PD1 expressing PD1 by screening.

2. Binding of Antibodies to 293T-PD1 Cell Surface Antigen

Antibody labeling and flow cytometry: The 293T-PD1 obtained by the step above was digested by trypsin, and distributed into tubes each containing $2 \times 10^5$ cells. PD1 antibodies was diluted using PBS buffer (1% BSA) at concentrations of 50 nM, 10 nM, 5 nM, 1 nM, 0.1 nM and 0.01 nM and added into the tubes and incubated on ice with PD1-expressing 293T cells for 2h. 100 L of FITC-labeled goat anti-human secondary antibody (1:500) was added into each tube and incubated on ice for 1h. After washed with PBS 3 times, cells were re-suspended in 300 μL of PBS and fluorescence signals were measured on the flow cytometer using the FITC channel.

Figure 7:
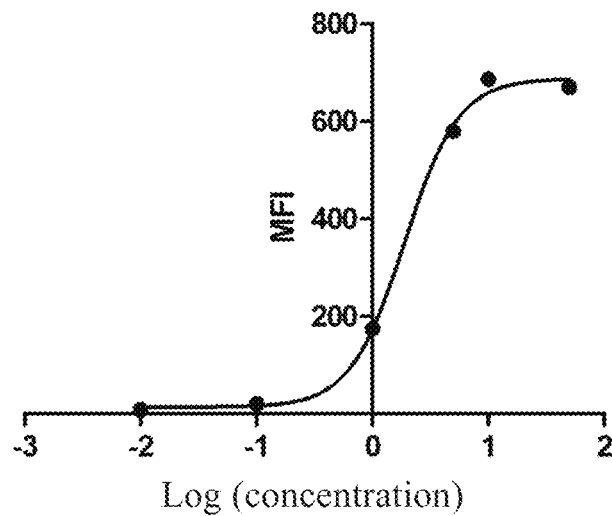
FIG. 7: $EC_{50}$ of 14C12H1L1 binding to PD1 on the Surface of 293T-PD1 Cells.

The binding results of the humanized antibody 14C12H1L1 to 293T-PD1 cells were shown in FIG. 7. As shown in FIG. 7, the antibody 14C12H1L1 can bind target PD1 protein expressing on the surface of host cells 293T-PD1 effectively with dose-dependency. The fluorescence intensities at different doses were shown in Table 4. Through Curve Simulation using quantitative analyses of fluorescence intensities, EC50 of 14C12H1L1 binding with PD1 was then determined to be 1.89 nM.

TABLE 4

The Fluorescence Intensities of 14C12H1L1 Binding to 293T-PD1 Surface Antigen Detected by Flow Cytometry

| Concentration (nM) | 0.01 | 0.1 | 1 | 5 | 10 | 50 |
|---|---|---|---|---|---|---|
| Fluorescence Intensity | 8.32 | 20.31 | 174.62 | 579.41 | 686.49 | 669.54 |

Example 9: Binding Activity of Antibody to T Cell Surface Antigen PD1 by Flow Cytometry PBMC was isolated by Ficoll-Paque Plus (GE Healthcare LOT No.: 171440-02), further isolated to get $CD4^+$ cells, and cells were stimulated with PHA (Shanghai Shenqi Biotech Co., Ltd, 50 μl/ml) for three days, and then washed once with PBS, and antibodies at different concentrations were added and incubated on ice for 1.5 h. The cells were then washed with PBS once after incubation, and the FITC-labeled goat anti-human secondary antibody (Jackson immunoresearch lot. 102155) was added and incubated on ice in the dark for 1h, and after washed with PBS once, the fluorescence signals were measured on the flow cytometer.

Figure 8:
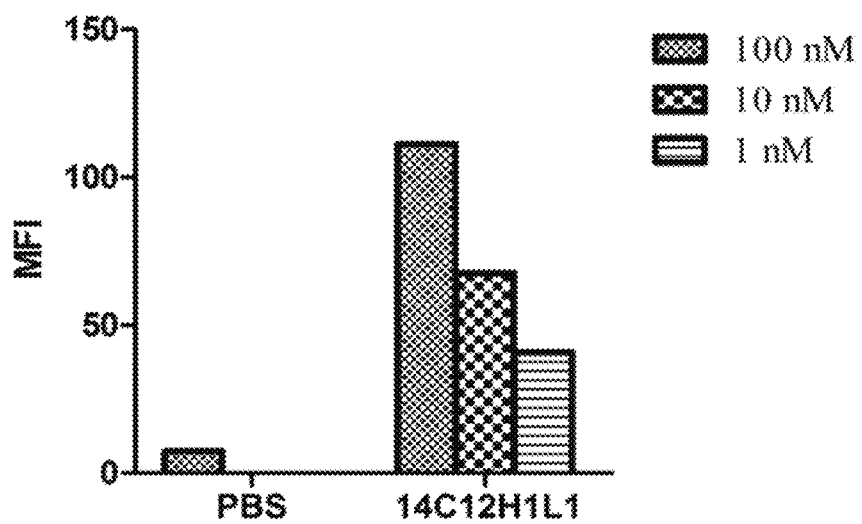
FIG. 8: Binding activity of 14C12H1L1 to T Cell Surface Antigen PD1.

The binding results of humanized antibody 14C12H1L1 to Tcells were shown in FIG. 8. Evidently, the antibody 14C12H1L1 can bind PD1 protein on T cell surface effectively with dose-dependency.

Example 10: Mixed Lymphocyte Reaction: Secretion of Cytokines IFN-γ, IL-2

PBMC was isolated by Ficoll-Paque Plus (GE Healthcare LOT No.: 171440-02), add the isolated PBMC was induced with IL-4 (Peprotech K2513, 1,000 U/ml) and GM-CSF (Peprotech H1513, 1,000 U/ml) for 6 days, and then TNF-α (Peprotech G1513, 200 U/ml) was added to induce for 3 days to obtain DC cells.

T cells were isolated from PBMC and mixed with the DC cells obtained above in the ratio of 10:1 to culture together with the antibodies 14C12H1L1, 5C4 and hIgG (hIgG as an isotype control) in different ratios for 5-6 days. The secretions of IFN-γ and IL-2 were measured with corresponding ELISA reagent kits (both purchased from Dakewe) respectively.

Figure 9:
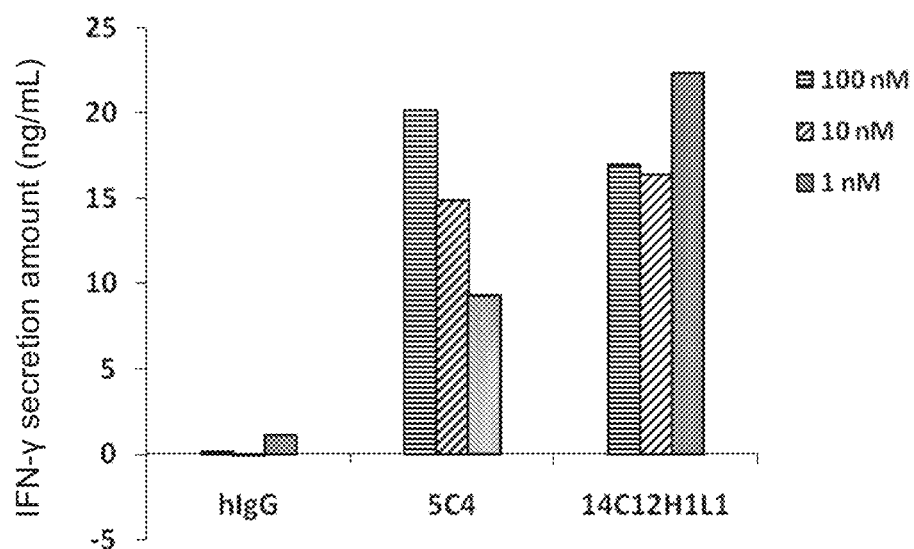
FIG. 9: Effect of 14C12H1L1 on IFN-7 Secretion of Mixed Lymphocytes.
Figure 10:
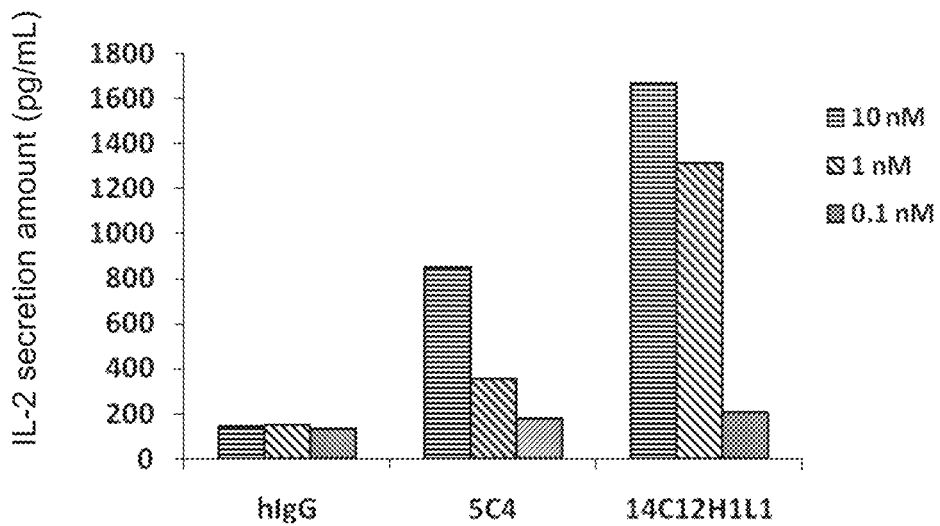
FIG. 10: Effect of 14C12H1L1 on IL-2 Secretion of Mixed Lymphocytes.

The secretions of IFN-γ and IL-2 after mixed culture of DC cells and T cells were shown in FIG. 9 and FIG. 10. 14C12H1L1 antibody can effectively induce the secretions of IFN-γ and IL-2 with dose-dependency. Antibody 14C12H1L1 can induce higher secretions of both IFN-γ and IL-2 than the control antibody 5C4.

Example 11: Induced IL-2 Secretion

The isolated PBMC (the same method as in Example 10) was stimulated with PHA (Shanghai Shenqi Biotech Co., Ltd, 50 μl/ml) for 3 days, and then mature PBMC ($5\times10^4$ cells/well) mixed with Raji cells (Chinese Academy of Sciences Shanghai Branch) ($5\times10^4$ cells/well) and MDA-MB-231 cells (ATCC) ($1\times10^4$ cells/well) in a 96-well plate. 100 nM of 14C12H1L1 or control antibody 5C4 or hIgG (hIgG as the isotype control) were added and mixed and cultured together for three days. The secretion of IL-2 was detected with ELISA reagent kit (purchased from Dakewe) according to the instructions of the kit.

Figure 11:
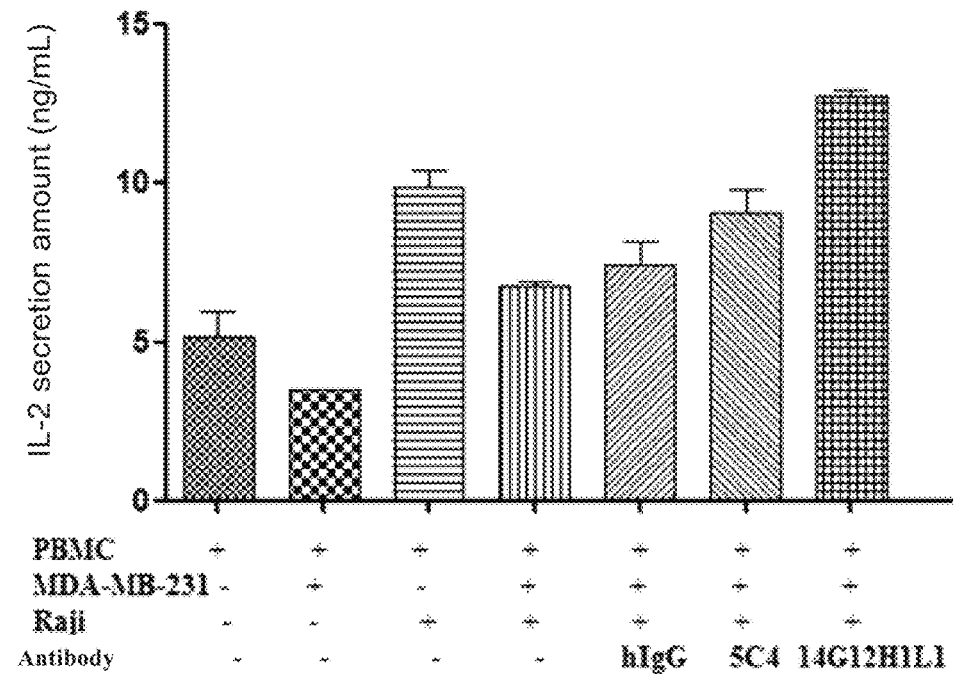
FIG. 11: Effect of 14C12H1L1 on the Secretion of Cytokine IL-2 Induced by Mixing PBMC, MDA-MB-231 and Raji Cells.

The results of IL-2 secretion after mixed cell culture were shown in FIG. 11. As shown in FIG. 11, antibody can effectively induce PBMC to secret IL-2, and the IL-2 secretion induced by 14C12H1L1 is significantly higher than that of control antibody 5C4.

Example 12: Impact of Antibody 14C12H1L1 on the Tumor Growth of MC38 Tumor Model in PD-1 HuGEMM Mice MC38 tumor cells ($1\times10^6$ cells/mouse) were inoculated subcutaneously on the right side of PD-1 HuGEMM mice (human PD-1 transgenic mice). When the mean tumor volume reached approximately 118 $mm^3$, the mice were randomly divided into 4 experimental groups with 8 mice in each group. Antibodies were given through abdominal administration. The specific grouping and dosages were as follows:

Isotype Control group (dose: 8 mg/kg),

14C12H1L1 high-dose group (dose: 8 mg/kg),

14C12H1L1 low-dose group (dose: 0.8 mg/kg),

Nivolumab group (dose: 8 mg/kg).

The above 4 groups were injected with antibodies twice weekly, 5 doses in total. After injection, the tumor sizes were measured twice weekly.

Figure 12:
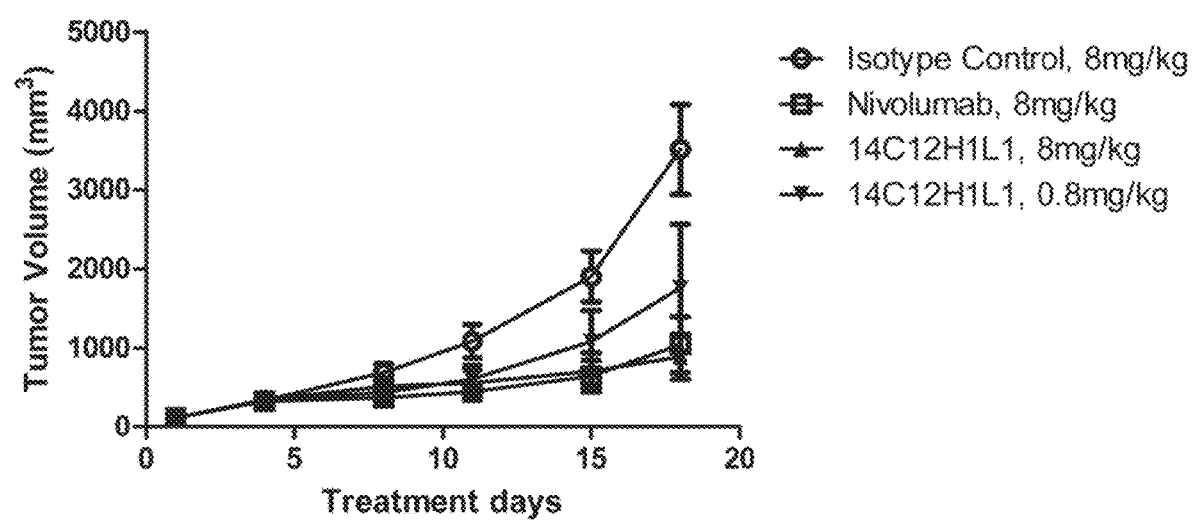
FIG. 12: Effect of 14C12H1L1 on the Tumor Growth of MC38 Tumor Model in PD-1 HuGEMM Mice.

The results were presented in FIG. 12.

The results indicating that:

The tumor sizes in the Nivolumab, 14C12H1L1 high-dose, and 14C12H1L1 low-dose groups were all significantly smaller than those in the Isotype control group statistically ($P<0.01$, $P<0.01$, $P<0.05$, respectively). 14C12H1L1 high-dose group (8 mg/kg) showed a statistically significant antitumor effect on the MC38 tumor model in the PD-1 HuGEMM mice, and had an efficacy equivalent to the approved drug for the same target, Nivolumab (8 mg/kg).

Although specific embodiments of the present invention have been described in detail, as will be appreciated by one skilled in the art, these details may incur various modifications and substitutions according to all the teachings we have disclosed. These changes are all covered by the scope of the present invention. The full scope of the present invention is given by the appended claims and any equivalents.

The invention claimed is:

1. A monospecific monoclonal antibody that binds to PD-1, comprising two heavy chains and two light chains, wherein:
   the variable region ($V_H$) of the heavy chain consists of the amino acid sequence as set forth in SEQ ID NO: 6 and the constant region of the heavy chain consists of the amino acid sequence as set forth in SEQ ID NO: 15; and
   the variable region ($V_L$) of the light chain consists of the amino acid sequence as set forth in SEQ ID NO: 8 and the constant region of the light chain consists of the amino acid sequence as set forth in SEQ ID NO: 16.

2. The monospecific monoclonal antibody of claim 1, wherein the monospecific monoclonal antibody has a binding affinity ($K_D$) to PD-1 that is less than $10^{-5}$ M.

3. An isolated polynucleotide comprising a sequence coding for the monospecific monoclonal antibody of claim 1.

4. An expression construct, wherein the expression construct comprises the isolated polynucleotide of claim 3.

5. An expression cell line, wherein the expression cell line comprises the isolated polynucleotide of claim 3.

6. A pharmaceutical composition comprising the monospecific monoclonal antibody of claim 1 and a pharmaceutically acceptable carrier or excipient.

* * * * *

SEQUENCE LISTING

<160> NUMBER OF SEQ ID NOS: 16

<210> SEQ ID NO 1
<211> LENGTH: 354
<212> TYPE: DNA
<213> ORGANISM: Artificial Sequence
<220> FEATURE:
<223> OTHER INFORMATION: monoclonal antibody 14C12 heavy chain variable
      region

<400> SEQUENCE: 1
gaggtcaaac tggtggagag cggcggcggg ctggtgaagc ccggcgggtc actgaaactg        60
agctgcgccg cttccggctt cgcctttagc tcctacgaca tgtcatgggt gaggcagacc       120
cctgagaagc gcctggaatg ggtcgctact atcagcggag cgggcgata cacctactat        180 cctgactctg tcaaagggag attcacaatt agtcgggata cgccagaaa tactctgtat        240 ctgcagatgt ctagtctgcg gtccgaggat acagctctgt actattgtgc aaaccggtac       300
ggcgaagcat ggtttgccta ttggggacag ggcaccctgg tgacagtctc tgcc             354

<210> SEQ ID NO 2
<211> LENGTH: 118
<212> TYPE: PRT
<213> ORGANISM: Artificial Sequence
<220> FEATURE:
<223> OTHER INFORMATION: monoclonal antibody 14C12 heavy chain variable
      region

<400> SEQUENCE: 2

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Thr Ile Ser Gly Gly Gly Arg Tyr Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
            85                  90                  95

Ala Asn Arg Tyr Gly Glu Ala Trp Phe Ala Tyr Trp Gly Gln Gly Thr
            100                 105                 110

Leu Val Thr Val Ser Ala
        115

<210> SEQ ID NO 3
<211> LENGTH: 318
<212> TYPE: DNA
<213> ORGANISM: Artificial Sequence
<220> FEATURE:
<223> OTHER INFORMATION: monoclonal antibody 14C12 light chain variable
      region

<400> SEQUENCE: 3
gacattaaga tgacacagtc cccttcctca atgtacgcta gcctgggcga gcgagtgacc        60
ttcacatgca aagcatccca ggacatcaac acatacctgt cttggtttca gcagaagcca       120
ggcaaaagcc ccaagaccct gatctaccgg gccaatagac tggtggacgg ggtccccagc       180
agattctccg gatctggcag tgggcaggat tactcccctga ccatcagctc cctggagtat      240
gaagacatgg gcatctacta ttgcctgcag tatgatgagt tccctctgac ctttggagca    300
ggcacaaaac tggaactg    318

<210> SEQ ID NO 4
<211> LENGTH: 106
<212> TYPE: PRT
<213> ORGANISM: Artificial Sequence
<220> FEATURE:
<223> OTHER INFORMATION: monoclonal antibody 14C12 light chain variable
      region

<400> SEQUENCE: 4

Asp Ile Lys Met Thr Gln Ser Pro Ser Ser Met Tyr Ala Ser Leu Gly
1               5                   10                  15

Glu Arg Val Thr Phe Thr Cys Lys Ala Ser Gln Asp Ile Asn Thr Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu
            100                 105

<210> SEQ ID NO 5
<211> LENGTH: 354
<212> TYPE: DNA
<213> ORGANISM: Artificial Sequence
<220> FEATURE:
<223> OTHER INFORMATION: monoclonal antibody 14C12H1L1 heavy chain
      variable region

<400> SEQUENCE: 5
gaagtgcagc tggtcgagtc tgggggaggg ctggtgcagc ccggcgggtc actgcgactg    60
agctgcgcag cttccggatt cgcctttagc tcctacgaca tgtcctgggt gcgacaggca    120
ccaggaaagg gactggattg ggtcgctact atctcaggag gcgggagata cacctactat    180
cctgacagcg tcaagggccg gttcacaatc tctagagata cagtaagaa caatctgtat    240 ctgcagatga acagcctgag ggctgaggac accgcactgt actattgtgc caaccgctac    300
ggggaagcat ggtttgccta ttgggggcag ggaaccctgg tgacagtctc tagt    354

<210> SEQ ID NO 6
<211> LENGTH: 118
<212> TYPE: PRT
<213> ORGANISM: Artificial Sequence
<220> FEATURE:
<223> OTHER INFORMATION: monoclonal antibody 14C12H1L1 heavy chain
      variable region

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Asp Trp Val
        35                  40                  45

```
Ala Thr Ile Ser Gly Gly Gly Arg Tyr Thr Tyr Tyr Pro Asp Ser Val
 50                  55                  60
Lys Gly Arg Phe Thr Ile Ser Arg Asp Asn Ser Lys Asn Asn Leu Tyr
 65                  70                  75                  80
Leu Gln Met Asn Ser Leu Arg Ala Glu Asp Thr Ala Leu Tyr Tyr Cys
                 85                  90                  95
Ala Asn Arg Tyr Gly Glu Ala Trp Phe Ala Tyr Trp Gly Gln Gly Thr
             100                 105                 110
Leu Val Thr Val Ser Ser
            115
```

<210> SEQ ID NO 7
<211> LENGTH: 321
<212> TYPE: DNA
<213> ORGANISM: Artificial Sequence
<220> FEATURE:
<223> OTHER INFORMATION: monoclonal antibody 14C12H1L1 light chain
      variable region

<400> SEQUENCE: 7

```
gacattcaga tgactcagag cccctcctcc atgtccgcct ctgtgggcga cagggtcacc      60
ttcacatgcc gcgctagtca ggatatcaac acctacctga ctggtttca gcagaagcca     120
gggaaaagcc ccaagacact gatctaccgg ctaatagac tggtgtctgg agtcccaagt     180
cggttcagtg gctcagggag cggacaggac tacactctga ccatcagctc cctgcagcct    240
gaggacatgg caacctacta ttgcctgcag tatgatgagt tcccactgac ctttggcgcc    300
gggacaaaac tggagctgaa g                                              321
```

<210> SEQ ID NO 8
<211> LENGTH: 107
<212> TYPE: PRT
<213> ORGANISM: Artificial Sequence
<220> FEATURE:
<223> OTHER INFORMATION: monoclonal antibody 14C12H1L1 light chain
      variable region

<400> SEQUENCE: 8

```
Asp Ile Gln Met Thr Gln Ser Pro Ser Ser Met Ser Ala Ser Val Gly
  1               5                  10                  15
Asp Arg Val Thr Phe Thr Cys Arg Ala Ser Gln Asp Ile Asn Thr Tyr
                 20                  25                  30
Leu Ser Trp Phe Gln Gln Lys Pro Gly Lys Ser Pro Lys Thr Leu Ile
             35                  40                  45
Tyr Arg Ala Asn Arg Leu Val Ser Gly Val Pro Ser Arg Phe Ser Gly
 50                  55                  60
Ser Gly Ser Gly Gln Asp Tyr Thr Leu Thr Ile Ser Ser Leu Gln Pro
 65                  70                  75                  80
Glu Asp Met Ala Thr Tyr Tyr Cys Leu Gln Tyr Asp Glu Phe Pro Leu
                 85                  90                  95
Thr Phe Gly Ala Gly Thr Lys Leu Glu Leu Lys
            100                 105
```

<210> SEQ ID NO 9
<211> LENGTH: 8
<212> TYPE: PRT
<213> ORGANISM: Artificial Sequence
<220> FEATURE:
<223> OTHER INFORMATION: heavy chain variable region CDR

<400> SEQUENCE: 9

```
Gly Phe Ala Phe Ser Ser Tyr Asp
1               5

<210> SEQ ID NO 10
<211> LENGTH: 8
<212> TYPE: PRT
<213> ORGANISM: Artificial Sequence
<220> FEATURE:
<223> OTHER INFORMATION: heavy chain variable region CDR

<400> SEQUENCE: 10

Ile Ser Gly Gly Gly Arg Tyr Thr
1               5

<210> SEQ ID NO 11
<211> LENGTH: 11
<212> TYPE: PRT
<213> ORGANISM: Artificial Sequence
<220> FEATURE:
<223> OTHER INFORMATION: heavy chain variable region CDR

<400> SEQUENCE: 11

Ala Asn Arg Tyr Gly Glu Ala Trp Phe Ala Tyr
1               5                   10

<210> SEQ ID NO 12
<211> LENGTH: 6
<212> TYPE: PRT
<213> ORGANISM: Artificial Sequence
<220> FEATURE:
<223> OTHER INFORMATION: light chain variable region CDR

<400> SEQUENCE: 12

Gln Asp Ile Asn Thr Tyr
1               5

<210> SEQ ID NO 13
<211> LENGTH: 3
<212> TYPE: PRT
<213> ORGANISM: Artificial Sequence
<220> FEATURE:
<223> OTHER INFORMATION: light chain variable region CDR

<400> SEQUENCE: 13

Arg Ala Asn
1

<210> SEQ ID NO 14
<211> LENGTH: 9
<212> TYPE: PRT
<213> ORGANISM: Artificial Sequence
<220> FEATURE:
<223> OTHER INFORMATION: light chain variable region CDR

<400> SEQUENCE: 14

Leu Gln Tyr Asp Glu Phe Pro Leu Thr
1               5

<210> SEQ ID NO 15
<211> LENGTH: 399
<212> TYPE: PRT
<213> ORGANISM: Homo sapiens

<400> SEQUENCE: 15

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Glu Leu Gln Leu Glu Glu Ser Cys
                325                 330                 335

Ala Glu Ala Gln Asp Gly Glu Leu Asp Gly Leu Trp Thr Thr Ile Thr
            340                 345                 350

Ile Phe Ile Thr Leu Phe Leu Leu Ser Val Cys Tyr Ser Ala Thr Val
        355                 360                 365

Thr Phe Phe Lys Val Lys Trp Ile Phe Ser Ser Val Val Asp Leu Lys
    370                 375                 380

Gln Thr Ile Ile Pro Asp Tyr Arg Asn Met Ile Gly Gln Gly Ala
385                 390                 395

<210> SEQ ID NO 16
<211> LENGTH: 107
<212> TYPE: PRT
<213> ORGANISM: Homo sapiens

```
<400> SEQUENCE: 16

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```